United States Patent [19]

Outtrup et al.

[11] Patent Number: 5,856,164
[45] Date of Patent: Jan. 5, 1999

[54] ALKALINE *BACILLUS AMYLASE*

[75] Inventors: Helle Outtrup; Henrik Bisgård-Frantzen; Peter Rahbek Østergaard; Michael Dolberg Rasmussen; Pia Van Der Zee, all of Bagsvaerd, Denmark

[73] Assignee: Novo Nordisk A/S, Bagsvaerd, Denmark

[21] Appl. No.: 861,837

[22] Filed: May 22, 1997

Related U.S. Application Data

[62] Division of Ser. No. 446,803, Jun. 1, 1995.

[30] Foreign Application Priority Data

| Mar. 29, 1994 | [DK] | Denmark | 353/94 |
| Nov. 3, 1994 | [DK] | Denmark | 1271/94 |
| Feb. 3, 1995 | [DK] | Denmark | 123/95 |

[51] Int. Cl.⁶ .............. C12N 9/28; C12N 1/20; C12N 15/00; C07H 21/04
[52] U.S. Cl. ............. 435/202; 435/252.3; 435/252.31; 435/252.33; 435/254.11; 435/320.1; 536/23.2; 935/22
[58] Field of Search ............... 435/204, 320.1, 435/252.5, 202, 252.3, 252.31, 252.33, 254.11; 536/23.2; 935/22

[56] References Cited

U.S. PATENT DOCUMENTS 5,364,782  11/1994  Quax et al. .................... 435/202

OTHER PUBLICATIONS

Tsukamoto et al. (1988) Nucleotide sequence of the maltohexaose amylase gene from an alkalophilic Bacillus sp #707 and structural similarity to liquifying type alpha amylases. Biochem. Biophys. Res. Commun. 151(1): 25–31, Feb. 29, 1988.

*Primary Examiner*—Robert A. Wax
*Assistant Examiner*—Einar Stole
*Attorney, Agent, or Firm*—Steve T. Zelson, Esq.; Cheryl H. Agris, Esq.

[57] ABSTRACT

An α-amylase characterized by having a specific activity at least 25% higher than the specific activity of Termamyl® at a temperature in the range of 25° C. to 55° C. and at a pH value in the range of pH 8 to pH 10.

13 Claims, 5 Drawing Sheets

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
( A ) LENGTH: 485 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 1:

```
His His Asn Gly Thr Asn Gly Thr Met Met Gln Tyr Phe Glu Trp Tyr
 1               5                  10                  15

Leu Pro Asn Asp Gly Asn His Trp Asn Arg Leu Arg Asp Ala Ala
             20                  25                  30

Asn Leu Lys Ser Lys Gly Ile Thr Ala Val Trp Ile Pro Pro Ala Trp
             35                  40                  45

Lys Gly Thr Ser Gln Asn Asp Val Gly Tyr Gly Ala Tyr Asp Leu Tyr
         50                  55                  60

Asp Leu Gly Glu Phe Asn Gln Lys Gly Thr Val Arg Thr Lys Tyr Gly
 65              70                  75                      80

Thr Arg Asn Gln Leu Gln Ala Ala Val Thr Ser Leu Lys Asn Asn Gly
                 85                  90                  95

Ile Gln Val Tyr Gly Asp Val Val Met Asn His Lys Gly Gly Ala Asp
             100                 105                 110

Gly Thr Glu Ile Val Asn Ala Val Glu Val Asn Arg Ser Asn Arg Asn
         115                 120                 125

Gln Glu Thr Ser Gly Glu Tyr Ala Ile Glu Ala Trp Thr Lys Phe Asp
     130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                 165                 170                 175

Ile Tyr Lys Phe Arg Gly Thr Gly Lys Ala Trp Asp Trp Glu Val Asp
             180                 185                 190

Thr Glu Asn Gly Asn Tyr Asp Tyr Leu Met Tyr Ala Asp Val Asp Met
         195                 200                 205

Asp His Pro Glu Val Ile His Glu Leu Arg Asn Trp Gly Val Trp Tyr
     210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                 245                 250                 255

Thr Gly Lys Pro Met Phe Ala Val Ala Glu Phe Trp Lys Asn Asp Leu
             260                 265                 270

Gly Ala Ile Glu Asn Tyr Leu Asn Lys Thr Ser Trp Asn His Ser Val
         275                 280                 285

Phe Asp Val Pro Leu His Tyr Asn Leu Tyr Asn Ala Ser Asn Ser Gly
     290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                 325                 330                 335

Gly Glu Ala Leu Glu Ser Phe Val Gln Gln Trp Phe Lys Pro Leu Ala
```

|   |   |   | 340 |   |   |   | 345 |   |   |   | 350 |   |   |
|---|---|---|---|---|---|---|---|---|---|---|---|---|---|
| Tyr | Ala | Leu<br>355 | Val | Leu | Thr | Arg | Glu<br>360 | Gln | Gly | Tyr | Pro<br>365 | Ser | Val | Phe | Tyr |
| Gly | Asp<br>370 | Tyr | Tyr | Gly | Ile | Pro<br>375 | Thr | His | Gly | Val | Pro<br>380 | Ala | Met | Lys | Ser |
| Lys<br>385 | Ile | Asp | Pro | Leu | Leu<br>390 | Gln | Ala | Arg | Gln | Thr<br>395 | Phe | Ala | Tyr | Gly | Thr<br>400 |
| Gln | His | Asp | Tyr | Phe<br>405 | Asp | His | His | Asp | Ile<br>410 | Ile | Gly | Trp | Thr | Arg<br>415 | Glu |
| Gly | Asn | Ser | Ser<br>420 | His | Pro | Asn | Ser | Gly<br>425 | Leu | Ala | Thr | Ile | Met<br>430 | Ser | Asp |
| Gly | Pro | Gly<br>435 | Gly | Asn | Lys | Trp | Met<br>440 | Tyr | Val | Gly | Lys | Asn<br>445 | Lys | Ala | Gly |
| Gln | Val<br>450 | Trp | Arg | Asp | Ile | Thr<br>455 | Gly | Asn | Arg | Thr | Gly<br>460 | Thr | Val | Thr | Ile |
| Asn<br>465 | Ala | Asp | Gly | Trp | Gly<br>470 | Asn | Phe | Ser | Val | Asn<br>475 | Gly | Gly | Ser | Val | Ser<br>480 |
| Val | Trp | Val | Lys | Gln<br>485 | | | | | | | | | | | |

(2) INFORMATION FOR SEQ ID NO: 2:

(i) SEQUENCE CHARACTERISTICS:
        (A) LENGTH: 485 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

| His<br>1 | His | Asn | Gly | Thr<br>5 | Asn | Gly | Thr | Met | Met<br>10 | Gln | Tyr | Phe | Glu | Trp<br>15 | His |
|---|---|---|---|---|---|---|---|---|---|---|---|---|---|---|---|
| Leu | Pro | Asn | Asp<br>20 | Gly | Asn | His | Trp | Asn<br>25 | Arg | Leu | Arg | Asp | Asp<br>30 | Ala | Ser |
| Asn | Leu | Arg<br>35 | Asn | Arg | Gly | Ile | Thr<br>40 | Ala | Ile | Trp | Ile | Pro<br>45 | Pro | Ala | Trp |
| Lys | Gly<br>50 | Thr | Ser | Gln | Asn | Asp<br>55 | Val | Gly | Tyr | Gly | Ala<br>60 | Tyr | Asp | Leu | Tyr |
| Asp<br>65 | Leu | Gly | Glu | Phe | Asn<br>70 | Gln | Lys | Gly | Thr | Val<br>75 | Arg | Thr | Lys | Tyr | Gly<br>80 |
| Thr | Arg | Ser | Gln | Leu<br>85 | Glu | Ser | Ala | Ile | His<br>90 | Ala | Leu | Lys | Asn | Asn<br>95 | Gly |
| Val | Gln | Val | Tyr<br>100 | Gly | Asp | Val | Val | Met<br>105 | Asn | His | Lys | Gly | Gly<br>110 | Ala | Asp |
| Ala | Thr | Glu<br>115 | Asn | Val | Leu | Ala | Val<br>120 | Glu | Val | Asn | Pro | Asn<br>125 | Asn | Arg | Asn |
| Gln | Glu<br>130 | Ile | Ser | Gly | Asp | Tyr<br>135 | Thr | Ile | Glu | Ala | Trp<br>140 | Thr | Lys | Phe | Asp |
| Phe<br>145 | Pro | Gly | Arg | Gly | Asn<br>150 | Thr | Tyr | Ser | Asp | Phe<br>155 | Lys | Trp | Arg | Trp<br>160 | Tyr |
| His | Phe | Asp | Gly | Val<br>165 | Asp | Trp | Asp | Gln | Ser<br>170 | Arg | Gln | Phe | Gln | Asn<br>175 | Arg |
| Ile | Tyr | Lys | Phe<br>180 | Arg | Gly | Asp | Gly | Lys<br>185 | Ala | Trp | Asp | Trp | Glu<br>190 | Val | Asp |
| Ser | Glu | Asn<br>195 | Gly | Asn | Tyr | Asp | Tyr<br>200 | Leu | Met | Tyr | Ala | Asp<br>205 | Val | Asp | Met |

```
Asp  His  Pro  Glu  Val  Val  Asn  Glu  Leu  Arg  Arg  Trp  Gly  Glu  Trp  Tyr
     210                     215                     220

Thr  Asn  Thr  Leu  Asn  Leu  Asp  Gly  Phe  Arg  Ile  Asp  Ala  Val  Lys  His
225                      230                     235                          240

Ile  Lys  Tyr  Ser  Phe  Thr  Arg  Asp  Trp  Leu  Thr  His  Val  Arg  Asn  Ala
               245                     250                          255

Thr  Gly  Lys  Glu  Met  Phe  Ala  Val  Ala  Glu  Phe  Trp  Lys  Asn  Asp  Leu
               260                     265                     270

Gly  Ala  Leu  Glu  Asn  Tyr  Leu  Asn  Lys  Thr  Asn  Trp  Asn  His  Ser  Val
               275                     280                     285

Phe  Asp  Val  Pro  Leu  His  Tyr  Asn  Leu  Tyr  Asn  Ala  Ser  Asn  Ser  Gly
     290                     295                     300

Gly  Asn  Tyr  Asp  Met  Ala  Lys  Leu  Leu  Asn  Gly  Thr  Val  Val  Gln  Lys
305                      310                     315                          320

His  Pro  Met  His  Ala  Val  Thr  Phe  Val  Asp  Asn  His  Asp  Ser  Gln  Pro
               325                     330                     335

Gly  Glu  Ser  Leu  Glu  Ser  Phe  Val  Gln  Glu  Trp  Phe  Lys  Pro  Leu  Ala
               340                     345                     350

Tyr  Ala  Leu  Ile  Leu  Thr  Arg  Glu  Gln  Gly  Tyr  Pro  Ser  Val  Phe  Tyr
               355                     360                     365

Gly  Asp  Tyr  Tyr  Gly  Ile  Pro  Thr  His  Ser  Val  Pro  Ala  Met  Lys  Ala
     370                     375                     380

Lys  Ile  Asp  Pro  Ile  Leu  Glu  Ala  Arg  Gln  Asn  Phe  Ala  Tyr  Gly  Thr
385                      390                     395                          400

Gln  His  Asp  Tyr  Phe  Asp  His  His  Asn  Ile  Ile  Gly  Trp  Thr  Arg  Glu
               405                     410                     415

Gly  Asn  Thr  Thr  His  Pro  Asn  Ser  Gly  Leu  Ala  Thr  Ile  Met  Ser  Asp
               420                     425                     430

Gly  Pro  Gly  Gly  Glu  Lys  Trp  Met  Tyr  Val  Gly  Gln  Asn  Lys  Ala  Gly
               435                     440                     445

Gln  Val  Trp  His  Asp  Ile  Thr  Gly  Asn  Lys  Pro  Gly  Thr  Val  Thr  Ile
     450                     455                     460

Asn  Ala  Asp  Gly  Trp  Ala  Asn  Phe  Ser  Val  Asn  Gly  Gly  Ser  Val  Ser
465                      470                     475                          480

Ile  Trp  Val  Lys  Arg
               485
```

(2) INFORMATION FOR SEQ ID NO: 3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

```
His  His  Asn  Gly  Thr  Asn  Gly  Thr  Met  Met  Gln  Tyr  Phe  Glu  Trp  Tyr
 1                  5                   10                          15

Leu  Pro  Asn  Asp
               20
```

(2) INFORMATION FOR SEQ ID NO: 4:

(i) SEQUENCE CHARACTERISTICS:
        (A) LENGTH: 1455 base pairs
        (B) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO: 4:

| | | | | | | |
|---|---|---|---|---|---|---|
| CATCATAATG | GAACAAATGG | TACTATGATG | CAATATTTCG | AATGGTATTT | GCCAAATGAC | 60 |
| GGGAATCATT | GGAACAGGTT | GAGGGATGAC | GCAGCTAACT | TAAAGAGTAA | AGGGATAACA | 120 |
| GCTGTATGGA | TCCCACCTGC | ATGGAAGGGG | ACTTCCCAGA | ATGATGTAGG | TTATGGAGCC | 180 |
| TATGATTTAT | ATGATCTTGG | AGAGTTTAAC | CAGAAGGGGA | CGGTTCGTAC | AAAATATGGA | 240 |
| ACACGCAACC | AGCTACAGGC | TGCGGTGACC | TCTTTAAAAA | ATAACGGCAT | TCAGGTATAT | 300 |
| GGTGATGTCG | TCATGAATCA | TAAAGGTGGA | GCAGATGGTA | CGGAAATTGT | AAATGCGGTA | 360 |
| GAAGTGAATC | GGAGCAACCG | AAACCAGGAA | ACCTCAGGAG | AGTATGCAAT | AGAAGCGTGG | 420 |
| ACAAAGTTTG | ATTTTCCTGG | AAGAGGAAAT | AACCATTCCA | GCTTTAAGTG | GCGCTGGTAT | 480 |
| CATTTTGATG | GGACAGATTG | GGATCAGTCA | CGCCAGCTTC | AAAACAAAAT | ATATAAATTC | 540 |
| AGGGGAACAG | GCAAGGCCTG | GGACTGGGAA | GTCGATACAG | AGAATGGCAA | CTATGACTAT | 600 |
| CTTATGTATG | CAGACGTGGA | TATGGATCAC | CCAGAAGTAA | TACATGAACT | TAGAAACTGG | 660 |
| GGAGTGTGGT | ATACGAATAC | ACTGAACCTT | GATGGATTTA | GAATAGATGC | AGTGAAACAT | 720 |
| ATAAAATATA | GCTTTACGAG | AGATTGGCTT | ACACATGTGC | GTAACACCAC | AGGTAAACCA | 780 |
| ATGTTTGCAG | TGGCTGAGTT | TTGGAAAAAT | GACCTTGGTG | CAATTGAAAA | CTATTTGAAT | 840 |
| AAAACAAGTT | GGAATCACTC | GGTGTTTGAT | GTTCCTCTCC | ACTATAATTT | GTACAATGCA | 900 |
| TCTAATAGCG | GTGGTTATTA | TGATATGAGA | AATATTTTAA | ATGGTTCTGT | GGTGCAAAAA | 960 |
| CATCCAACAC | ATGCCGTTAC | TTTTGTTGAT | AACCATGATT | CTCAGCCCGG | GGAAGCATTG | 1020 |
| GAATCCTTTG | TTCAACAATG | GTTTAAACCA | CTTGCATATG | CATTGGTTCT | GACAAGGGAA | 1080 |
| CAAGGTTATC | CTTCCGTATT | TTATGGGGAT | TACTACGGTA | TCCCAACCCA | TGGTGTTCCG | 1140 |
| GCTATGAAAT | CTAAAATAGA | CCCTCTTCTG | CAGGCACGTC | AAACTTTTGC | CTATGGTACG | 1200 |
| CAGCATGATT | ACTTTGATCA | TCATGATATT | ATCGGTTGGA | CAAGAGAGGG | AAATAGCTCC | 1260 |
| CATCCAAATT | CAGGCCTTGC | CACCATTATG | TCAGATGGTC | CAGGTGGTAA | CAAATGGATG | 1320 |
| TATGTGGGGA | AAAATAAAGC | GGGACAAGTT | TGGAGAGATA | TTACCGGAAA | TAGGACAGGC | 1380 |
| ACCGTCACAA | TTAATGCAGA | CGGATGGGGT | AATTTCTCTG | TTAATGGAGG | GTCCGTTTCG | 1440 |
| GTTTGGGTGA | AGCAA | | | | | 1455 |

(2) INFORMATION FOR SEQ ID NO: 5:

(i) SEQUENCE CHARACTERISTICS:
(A) LENGTH: 1455 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 5:

| | | | | | | |
|---|---|---|---|---|---|---|
| CATCATAATG | GGACAAATGG | GACGATGATG | CAATACTTTG | AATGGCACTT | GCCTAATGAT | 60 |
| GGGAATCACT | GGAATAGATT | AAGAGATGAT | GCTAGTAATC | TAAGAAATAG | AGGTATAACC | 120 |
| GCTATTTGGA | TTCCGCCTGC | CTGGAAAGGG | ACTTCGCAAA | ATGATGTGGG | GTATGGAGCC | 180 |
| TATGATCTTT | ATGATTTAGG | GGAATTTAAT | CAAAAGGGGA | CGGTTCGTAC | TAAGTATGGG | 240 |
| ACACGTAGTC | AATTGGAGTC | TGCCATCCAT | GCTTTAAAGA | ATAATGGCGT | TCAAGTTTAT | 300 |

| | | | | | | |
|---|---|---|---|---|---|---|
| GGGGATGTAG | TGATGAACCA | TAAAGGAGGA | GCTGATGCTA | CAGAAAACGT | TCTTGCTGTC | 360 |
| GAGGTGAATC | CAAATAACCG | GAATCAAGAA | ATATCTGGGG | ACTACACAAT | TGAGGCTTGG | 420 |
| ACTAAGTTTG | ATTTTCCAGG | GAGGGGTAAT | ACATACTCAG | ACTTTAAATG | GCGTTGGTAT | 480 |
| CATTTCGATG | GTGTAGATTG | GGATCAATCA | CGACAATTCC | AAAATCGTAT | CTACAAATTC | 540 |
| CGAGGTGATG | GTAAGGCATG | GGATTGGGAA | GTAGATTCGG | AAAATGGAAA | TTATGATTAT | 600 |
| TTAATGTATG | CAGATGTAGA | TATGGATCAT | CCGGAGGTAG | TAAATGAGCT | TAGAAGATGG | 660 |
| GGAGAATGGT | ATACAAATAC | ATTAAATCTT | GATGGATTTA | GGATCGATGC | GGTGAAGCAT | 720 |
| ATTAAATATA | GCTTACACG | TGATTGGTTG | ACCCATGTAA | GAAACGCAAC | GGGAAAAGAA | 780 |
| ATGTTTGCTG | TTGCTGAATT | TTGGAAAAAT | GATTTAGGTG | CCTTGGAGAA | CTATTTAAAT | 840 |
| AAAACAAACT | GGAATCATTC | TGTCTTTGAT | GTCCCCCTTC | ATTATAATCT | TTATAACGCG | 900 |
| TCAAATAGTG | GAGGCAACTA | TGACATGGCA | AAACTTCTTA | ATGGAACGGT | TGTTCAAAAG | 960 |
| CATCCAATGC | ATGCCGTAAC | TTTTGTGGAT | AATCACGATT | CTCAACCTGG | GGAATCATTA | 1020 |
| GAATCATTTG | TACAAGAATG | GTTAAGCCA | CTTGCTTATG | CGCTTATTTT | AACAAGAGAA | 1080 |
| CAAGGCTATC | CCTCTGTCTT | CTATGGTGAC | TACTATGGAA | TTCCAACACA | TAGTGTCCCA | 1140 |
| GCAATGAAAG | CCAAGATTGA | TCCAATCTTA | GAGGCGCGTC | AAAATTTTGC | ATATGGAACA | 1200 |
| CAACATGATT | ATTTTGACCA | TCATAATATA | ATCGGATGGA | CACGTGAAGG | AAATACCACG | 1260 |
| CATCCCAATT | CAGGACTTGC | GACTATCATG | TCGGATGGGC | CAGGGGAGA | GAAATGGATG | 1320 |
| TACGTAGGGC | AAAATAAAGC | AGGTCAAGTT | TGGCATGACA | TAACTGGAAA | TAAACCAGGA | 1380 |
| ACAGTTACGA | TCAATGCAGA | TGGATGGGCT | AATTTTTCAG | TAAATGGAGG | ATCTGTTTCC | 1440 |
| ATTTGGGTGA | AACGA | | | | | 1455 |

ALKALINE BACILLUS AMYLASE

This application is a divisional application of co-pending application Ser. No. 08/446,803 filed as PCT/DK95/00142, Mar. 29, 1995 and claims priority of Danish application Ser. Nos. 353/94 filed on 29 Mar. 1994 in Denmark; 1271/94 filed on 3 Nov. 1994 in Denmark; and 123/95 filed on 3 Feb. 1995 in Denmark the contents of which are fully incorporated herein by reference in their entirety.

FIELD OF INVENTION

The present invention relates to amylases having improved dishwashing and/or washing performance.

BACKGROUND OF THE INVENTION

For a number of years a-amylase enzymes have been used for a variety of different purposes, the most important of which are starch liquefaction, textile desizing, starch modification in the paper and pulp industry, and for brewing and baking. A further use of α-amylases, which is becoming increasingly important is the removal of starchy stains during washing and dishwashing.

Examples of commercial α-amylase products are Termamyl®, BAN® and Fungamyl®, all available from Novo Nordisk A/S, Denmark. These and similar products from other commercial sources have an acidic to a neutral pH optimum, typically in the range of from pH 5 to pH 7.5, which means that they do not display optimal activity in detergent solutions owing to the alkaline character of the detergents.

It is an object of the present invention to provide novel α-amylases with improved performance in alkaline solutions, especially in alkaline detergent solutions.

SUMMARY OF THE INVENTION

The present invention provides α-amylases with a very high specific activity at pH 8–10 and at temperatures of from 30° C. to around 60° C., conditions normal in detergent solutions.

Accordingly, the present invention relates to an α-amylase having a specific activity at least 25% higher than the specific activity of Termamyl® at a temperature in the range of 25° C. to 55° C. and at a pH value in the range of pH 8 to pH 10, measured by the α-amylase activity assay as described herein.

BRIEF DESCRIPTION OF DRAWINGS

The present invention is further illustrated with reference to the accompanying drawings, in which.

DETAILED DESCRIPTION OF THE INVENTION

The α-Amylases of the Invention

Figure 1:
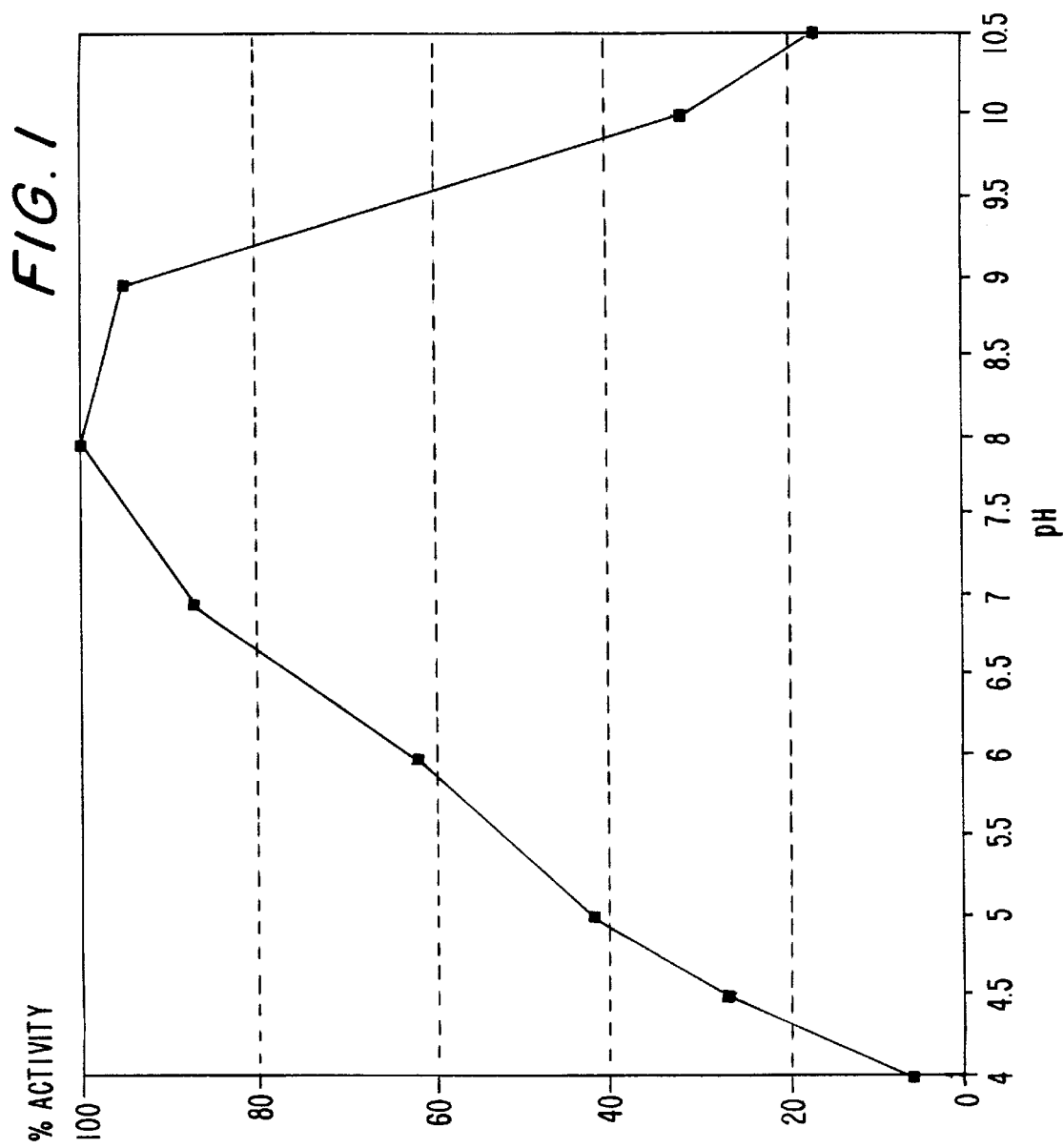
FIG. 1 shows the relation between pH and the α-amylase activity of a novel amylase (obtained from Bacillus strain NCIB 12289), determined as described in Example 2.

One embodiment of the present invention provides an α-amylase having a specific activity at least 25% higher or at least 35% higher or at least 45% higher or at least 55% higher or at least 65% higher or at least 75% or at least 25–75% higher than the specific activity of Termamyl® at a temperature in the range of 25° C. to 55° C. or at a temperature in the range of 25° C. to 35° C. or at a temperature in the range of 35° C. to 45° C. or at a temperature in the range of 45° C. to 55° C. and at a pH value in the range of pH 8 to pH 10 or at a pH value in the range of pH 8 to 8.5 or at a pH value in the range of pH 8.5 to 9.0 or at a pH value in the range of pH 9.0 to 9.5 or at a pH value in the range of pH 9.5 to 10.0, measured by the α-amylase activity assay as described herein.

It has surprisingly been found that preferred novel α-amylases of the invention may be characterized by having a specific activity at least 25% higher than the specific activity of Termamyl® at any temperature in the range of 25° C. to 55° C. and at any pH value in the range of from pH 8 to pH 10, measured by the α-amylase activity assay as described herein.

Compared with known α-amylases it is very remarkable how well the α-amylases of the invention perform at pH 10; accordingly in a preferred embodiment the α-amylase is characterized by having a specific activity at least 25% higher than the specific activity of Termamyl® at any temperature in the range of 25° C. to 55° C. and at pH 10, using the α-amylase activity assay as described herein.

In another aspect the invention relates to an α-amylase comprising the amino acid sequence shown in SEQ ID No. 1 or an α-amylase being at least 80% homologous with the amino acid sequence (SEQ ID No.1), preferably being at least 85% homologous with SEQ ID No. 1, more preferably being at least 90% homologous with SEQ ID No. 1.

A polypeptide is considered to be X% homologous to the parent α-amylase if a comparison of the respective amino acid sequences, performed via known algorithms, such as the one described by Lipman and Pearson in *Science* 227, 1985, p. 1435, reveals an identity of X%.

In a further aspect the invention relates to an α-amylase comprising the amino acid sequence shown in SEQ ID No. 2 or an α-amylase being at least 80% homologous with the amino acid sequence (SEQ ID No.2), preferably being at least 85% homologous with SEQ ID No. 2, more preferably being at least 90% homologous with SEQ ID No.2.

In another embodiment the invention relates to an α-amylase comprising an N-terminal amino acid sequence identical to that shown in SEQ ID No. 3 or an α-amylase being at least 80% homologous with SEQ ID No.3 in the N-terminal, preferably being at least 90% homologous with SEQ ID No.3 in the N-terminal.

Preferred α-amylases of the invention are obtainable from an alkaliphilic Bacillus species, particularly from one of the Bacillus strains NCIB 12289, NCIB 12512, NCIB 12513 and DSM 9375. In the context of the present invention, the term "obtainable from" is intended not only to indicate an α-amylase produced by a Bacillus strain but also an α-amylase encoded by a DNA sequence isolated from such a Bacillus strain and produced in a host organism transformed with said DNA sequence.

The strain NCIB 12289 is described in detail in EP 0 277 216. The strain NCIB 12289 has been deposited according to the Budapest Treaty on the International Recognition of the Deposits of Microorganisms for the Purpose of Patent Procedures, on 8 July 1986 at The National Collection of Industrial Bacteria (NCIB) under accession no. NCIB 12289.

The strain NCIB 12512 is described in detail in EP 0 277 216. The strain NCIB 12512 has been deposited according to the Budapest Treaty on the International Recognition of the Deposits of Microorganisms for the Purpose of Patent Procedures, on 5 Aug. 1987 at The National Collection of Industrial Bacteria (NCIB) under accession no. NCIB 12512.

The strain NCIB 12513 is described in detail in EP 0 277 216. The strain NCIB 12513 has been deposited according to the Budapest Treaty on the International Recognition of the Deposits of Microorganisms for the Purpose of Patent Procedures, on 5 Aug. 1987 at The National Collection of Industrial Bacteria (NCIB) under accession no. NCIB 12513.

The strain DSM 9375 has been deposited according to the Budapest Treaty on the International Recognition of the Deposits of Microorganisms for the Purpose of Patent Procedures, on 16 Aug. 1994 at Deutsche Sammlung von Mikroorganismen und Zellkulturen GmbH (DSM) under Accession No. DSM 9375.

Cloning a DNA Sequence Encoding an α-amylase

The DNA sequence encoding an α-amylase of the invention may be isolated from any cell or microorganism producing the α-amylase in question, using various methods well known in the art. First, a genomic DNA and/or cDNA library should be constructed using chromosomal DNA or messenger RNA from the organism that produces the α-amylase to be studied. Then, if the amino acid sequence of the α-amylase is known, homologous, labelled oligonucleotide probes may be synthesized and used to identify α-amylase-encoding clones from a genomic library prepared from the organism in question. Alternatively, a labelled oligonucleotide probe containing sequences homologous to a known α-amylase gene could be used as a probe to identify α-amylase-encoding clones, using hybridization and washing conditions of lower stringency. According to the present invention preferred probes may be constructed on the basis of SEQ ID No. 1 or on the basis of SEQ ID No. 2 or on the basis of SEQ ID No. 4 or on the basis of SEQ ID No 5.

Yet another method for identifying α-amylase-encoding clones would involve inserting fragments of genomic DNA into an expression vector, such as a plasmid, transforming α-amylase-negative bacteria with the resulting genomic DNA library, and then plating the transformed bacteria onto agar containing a substrate for α-amylase, thereby allowing clones expressing the α-amylase to be identified.

Alternatively, the DNA sequence encoding the enzyme may be prepared synthetically by established standard methods, e.g. the phosphoamidite method described by S. L. Beaucage and M. H. Caruthers in *Tetrahedron Letters* 22, 1981, pp. 1859–1869 or the method described by Matthes et al. in *The EMBO J.* 3, 1984, pp. 801–805. In the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. in *Science* 239, 1988, pp. 487–491.

Expression of α-amylase

According to the invention, an α-amylase-encoding DNA sequence produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an α-amylase of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome (s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding an α-amylase of the invention, especially in a bacterial host, are the promoter of the lac operon of *E.coli*, the *Streptomyces coelicolor* agarase gene dagA promoters, the promoters of the Bacillus licheniformis α-amylase gene (amyL), the promoters of the *Bacillus stearothermophilus* maltogenic amylase gene (amyM), the promoters of the Bacillus Amylolicuefaciens α-amylase (amyO), the promoters of the *Bacillus subtilis* xylA and xylB genes etc. For transcription in a fungal host, examples of useful promoters are those derived from the gene encoding *A. orvzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the α-amylase of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g., a gene the product of which complements a defect in the host cell, such as the dal genes from *B. subtilis* or *B. licheniformis,* or one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular.

Procedures suitable for constructing vectors of the invention encoding an α-amylase and containing the promoter, terminator and other elements, respectively, are well known to persons skilled in the art (cf., for instance, Sambrook et al. in *Molecular Cloning: A Laboratory Manual,* 2nd Ed., Cold Spring Harbor, 1989).

The cell of the invention, either comprising a DNA construct or an expression vector of the invention as defined above, is advantageously used as a host cell in the recombinant production of an α-amylase of the invention. The cell may be transformed with the DNA construct of the invention encoding the α-amylase conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g.., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are grampositive bacteria such as *Bacillus subtilis, Bacillus licheniformis, Bacillus lentus, Bacillus brevis, Bacillus stearothermophilus, Bacillus alkalophilus, Bacillus amylolicuefaciens, Bacillus coaculans, Bacillus circulans, Bacillus lautus, Bacillus meaterium, Bacillus thurinciensis,* or *Streptomyces lividans* or *Streptomyces murinus,* or gramnegative bacteria such as *E.coli.*

The transformation of the bacteria may, for instance, be effected by protoplast transformation or by using competent cells in a manner known per se.

The yeast organism may favourably be selected from a species of Saccharomyces or Schizosaccharomyces, e.g., *Saccharomyces cerevisiae.* The filamentous fungus may advantageously belong to a species of Aspergillus, e.g., *Aspergillus oryzae* or *Aspergillus niger.* Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing an α-amylase of the invention, which method comprises cultivating a host cell as described above under conditions conducive to the production of the α-amylase and recovering the α-amylase from the cells and/or culture medium.

The medium used to cultivate the cells may be any conventional medium suitable for growing the host cell in question and obtaining expression of the α-amylase of the invention. Suitable media are available from commercial suppliers or may be prepared according to published recipes (e.g., as described in catalogues of the American Type Culture Collection).

The α-amylase secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Assay for α-Amylase Activity

α-Amylase activity was determined by a method employing Phadebas® tablets as substrate. Phadebas tablets (Phadebas® Amylase Test, supplied by Pharmacia Diagnostic) contain a cross-linked insoluble blue-coloured starch polymer which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$ pH adjusted to the value of interest with NaOH). The test is performed in a water bath at the temperature of interest. The α-amylase to be tested is diluted in x ml of 50 mM Britton-Robinson buffer. 1 ml of this α-amylase solution is added to the 5 ml 50 mM Britton-Robinson buffer. The starch is hydrolysed by the α-amylase giving soluble blue fragments. The absorbance of the resulting blue solution, measured spectrophotometrically at 620 nm, is a function of the α-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion.

Under a specified set of conditions (temp.; pH, reaction time, buffer conditions) 1 mg of a given α-amylase will hydrolyse a certain amount of substrate and a blue colour will be produced. The colour intensity is measured at 620 nm. The measured absorbance is directly proportional to the specific activity (activity/mg of pure α-amylase protein) of the α-amylase in question under the given set of conditions. Thus, by testing different α-amylases of interest (including Termamyl®, the α-amylase used for reference) under identical conditions, the specific activity of each of the α-amylases at a given temperature and at a given pH can be compared directly, and the ratio of the specific activity of each of the α-amylases of interest relative to the specific activity of Termamyl® can be determined.

Industrial Applications

Owing to their activity at alkaline pH values, the α-amylases of the invention are well suited for use in a variety of industrial processes, in particular the enzyme finds potential applications as a component in washing, dishwashing and hard surface cleaning detergent compositions, but it may also be useful in the production of sweeteners and ethanol from starch. Conditions for conventional starch-converting processes and liquefaction and/or saccharification processes are described in, for instance, U.S. Pat. No. 3,912,590 and EP patent publications Nos. 252,730 and 63,909.

Being alkaline the α-amylases of the invention also possess valuable properties in the production of lignocellulosic materials, such as pulp, paper and cardboard, from starch reinforced waste paper and cardboard, especially where repulping occurs at pH above 7 and where amylases can facilitate the disintegration of the waste material through degradation of the reinforcing starch. The α-amylases of the invention are especially useful in the deinking/recycling processes of making paper out of old starch-coated or starch-containing printed paper. It is usually desirable to remove the printing ink in order to produce new paper of high brightness; examples of how the α-amylases of the invention may be used in this way are described in PCT/DK 94/00437.

The α-amylases of the invention may also be very useful in modifying starch where enzymatically modified starch is used in papermaking together with alkaline fillers such as calcium carbonate, kaolin and clays. With the alkaline α-amylases of the invention it becomes possible to modify the starch in the presence of the filler thus allowing for a simpler integrated process.

The α-amylases of the invention may also be very useful in textile desizing. In the textile processing industry, α-amylases are traditionally used as auxiliaries in the desizing process to facilitate the removal of starch-containing size which has served as a protective coating on weft yarns during weaving.

Complete removal of the size coating after weaving is important to ensure optimum results in the subsequent processes, in which the fabric is scoured, bleached and dyed. Enzymatic starch break-down is preferred because it does not involve any harmful effect on the fibre material.

In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional α-amylases are not very compatible with high pH levels and bleaching agents. The non-enzymatic breakdown of the starch size does lead to some fibre damage because of the rather aggressive chemicals used.

Accordingly, it would be desirable to use the α-amylases of the invention as they have an improved performance in alkaline solutions. The α-amylases may be used alone or in combination with a cellulase when desizing cellulose-containing fabric or textile.

The α-amylases of the invention may also be very useful in a beer-making process; the α-amylases will typically be added during the mashing process.

Detergent Compositions

According to the invention, the α-amylases may typically be a component of a detergent composition, e.g., a laundry detergent composition or a dishwashing detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or amphoteric (zwitterionic). The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), alcohol propoxylate, carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as pullulanase, esterase, lipase, cutinase, protease, cellulase, peroxidase, or oxidase, e.g., laccase.

Normally the detergent contains 1–65% of a detergent builder, but some dishwashing detergents may contain even up to 90% of a detergent builder, or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst).

The detergent builders may be subdivided into phosphorus-containing and non-phosphorous-containing types. Examples of phosphorus-containing inorganic alkaline detergent builders include the water-soluble salts, especially alkali metal pyrophosphates, orthophosphates, polyphosphates and phosphonates. Examples of non-phosphorus-containing inorganic builders include water-soluble alkali metal carbonates, borates and silicates as well as layered disilicates and the various types of water-insoluble crystalline or amorphous alumino silicates of which zeolites is the best known representative.

Examples of suitable organic builders include alkali metal, ammonium or substituted ammonium salts of succinates, malonates, fatty acid malonates, fatty acid sulphonates, carboxymethoxy succinates, polyacetates, carboxylates, polycarboxylates, aminopolycarboxylates and polyacetyl carboxylates.

The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, polymaleates, maleic/acrylic acid copolymers and lauryl methacrylate/acrylic acid copolymers.

The detergent composition may contain bleaching agents of the chlorine/bromine-type or the oxygen-type. The bleaching agents may be coated or incapsulated. Examples of inorganic chlorine/bromine-type bleaches are lithium, sodium or calcium hypochlorite or hypobromite as well as chlorinated trisodium phosphate. The bleaching system may also comprise a $H_2O_2$ source such as perborate or percarbonate which may be combined with a peracid-forming bleach activator such as tetraacetylethylenediamine (TAED) or nonanoyloxybenzenesulfonate (NOBS).

Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water solubilizing cations such as potassium and sodium. Hydantoin compounds are also suitable. The bleaching system may also comprise peroxyacids of, e.g., the amide, imide, or sulfone type.

In dishwashing detergents the oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates Preferred activator materials are TAED or NOBS.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708. The enzymes of the invention may also be stabilized by adding reversible enzyme inhibitors, e.g., of the protein type as described in EP 0 544 777 B1.

The detergent may also contain other conventional detergent ingredients such as, e.g., fabric conditioners including clays, deflocculant material, foam boosters/foam depressors (in dishwashing detergents foam depressors), suds suppressors, anti-corrosion agents, soil-suspending agents, anti-soil-redeposition agents, dyes, dehydrating agents, bactericides, optical brighteners, or perfume.

The pH (measured in aqueous solution at use concentration) will usually be neutral or alkaline, e.g. in the range of 7–11.

Particular forms of laundry detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g. $C_{12-18}$ alcohol, 1–2 EO) or alkyl sulfate (e.g. $C_{16-18}$) | 1–4% |
| Alcohol ethoxylate (e.g. $C_{14-15}$ alcohol, 7 EO) | 5–9% |
| Sodium carbonate (as $Na_2CO_3$) | 14–20% |
| Soluble silicate (as $Na_2O, 2SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_4H_5Na_3O_7/C_6H_8O_7$) | 0–15% |
| Sodium perborate (as $NaBO_3.H_2O$) | 11–18% |
| TAED | 2–6% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g. $C_{12-18}$ alcohol, 1–2 EO or alkyl sulfate (e.g. $C_{16-18}$) | 1–3% |
| Alcohol ethoxylate (e.g. $C_{14-15}$ alcohol, 7 EO) | 5–9% |
| Sodium carbonate (as $Na_2CO_3$) | 15–21% |
| Soluble silicate (as $Na_2O, 2SiO_2$) | 1–4% |
| Zeolite (as $NaAlSiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethylcellulose | 0–2% |
| Polymers (e.g. maleic/acrylic acid copolymer, PVP, PEG) | 1–6% |
| Enzymes (calculated as pure enzyme protein) | 0.0001–0.1% |
| Minor ingredients (e.g. suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g. $C_{12-15}$ alcohol, 7 EO) | 7–14% |
| Soap as fatty acid (e.g. $C_{16-22}$ fatty acid) | 1–3% |
| Sodium carbonate (as $Na_2CO_3$) | 10–17% |
| Soluble silicate (as $Na_2O, 2SiO_2$) | 3–9% |
| Zeolite (as $NaAlSiO_4$) | 23–33% |
| Sodium sulfate (as $Na_2SO4$) | 0–4% |
| Sodium perborate (as $NaBO_3.H_2O$) | 8–16% |
| TAED | 2–8% |
| Phosphonate (e.g. EDTMPA) | 0–1% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |

-continued

| | |
|---|---|
| Alcohol ethoxylate (e.g. $C_{12-15}$ alcohol, 7 EO) | 10–25% |
| Sodium carbonate (as $Na_2CO_3$) | 14–22% |
| Soluble silicate (as $Na_2O, 2SiO_2$) | 1–5% |
| Zeolite (as $NaAlSiO_4$) | 25–35% |
| Sodium sulfate (as $Na_2SO_4$) | 0–10% |
| Carboxymethylcellulose | 0–2% |
| Polymers (e.g. maleic/acrylic acid copolymer, PVP, PEG) | 1–3% |
| Enzymes (calculated as pure enzyme protein) | 0.0001–0.1% |
| Minor ingredients (e.g. suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO or $C_{12-15}$ alcohol, 5 EO) | 12–18% |
| Soap as fatty acid (e.g. oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g. PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g. dispersants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO, or $C_{12-15}$ alcohol, 5 EO) | 3–9% |
| Soap as fatty acid (e..g. oleic acid) | 3–10% |
| Zeolite (as $NaAlSiO_4$) | 14–22% |
| Potassium citrate | 9–18% |
| Borate (as $B_4O_7$) | 0–2% |
| Carboxymethylcellulose | 0–2% |
| Polymers (e.g. PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g. dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O, 2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g. maleic/acrylic acid copolymer, PEG) | 1–5% |
| Enzymes (calculated as pure enzyme protein) | 0.0001–0.1% |
| Minor ingredients (e.g. optical brightener, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O, 2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g. PVP, maleic/acrylic acid copolymer, PEG) | 1–5% |
| Enzymes (calculated as pure enzyme protein) | 0.0001–0.1% |
| Minor ingredients (e.g. suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |
| Bleach activator (e.g. NOBS or TAED) | 1–5% |
| Carboxymethylcellulose | 0–2% |
| Polymers (e.g. polycarboxylate or PEG) | 1–5% |
| Enzymes (calculated as pure enzyme protein) | 0.0001–0.1% |
| Minor ingredients (e.g. optical brightener, perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g. $C_{12-15}$ alcohol, 2–3 EO) | 8–15% |
| Alcohol ethoxylate (e.g. $C_{12-15}$ alcohol, 7 EO, or $C_{12-15}$ alcohol, 5 EO) | 3–9% |
| Soap as fatty acid (e.g. lauric acid) | 0–3% |
| Aminoethanol | 1–5% |
| Sodium citrate | 5–10% |
| Hydrotrope (e.g. sodium toluensulfonate) | 2–6% |
| Borate (as $B_4O_7$) | 0–2% |
| Carboxymethylcellulose | 0–1% |

-continued

| Ethanol | 1–3% |
| Propylene glycol | 2–5% |
| Enzymes (calculated as pure enzyme protein) | 0.0001–0.1% |
| Minor ingredients (e.g. polymers, dispersants, perfume, optical brighteners) | 0–5% |

11) An aqueous liquid detergent composition comprising

| Linear alkylbenzenesulfonate (calculated as acid) | 20–32% |
| Alcohol ethoxylate (e.g. $C_{12-15}$ alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g. maleic/acrylic acid copolymer, anchoring polymer such as, e.g., lauryl methacrylate/acrylic acid copolymer) | 0–3% |
| Glycerol | 3–8% |
| Enzymes (calculated as pure enzyme protein) | 0.0001–0.1% |
| Minor ingredients (e.g. hydrotropes, dispersants, perfume, optical brighteners) | 0–5% |

12) A detergent composition formulated as a granulate having a bulk density of at least 600 g/l comprising

| Anionic surfactant (linear alkylbenzenesulfonate, alkyl sulfate, alpha-olefinsulfonate, alpha-sulfo fatty acid methyl esters, alkanesulfonates, soap) | 25–40% |
| Nonionic surfactant (e.g. alcohol ethoxylate) | 1–10% |
| Sodium carbonate (as $Na_2CO_3$) | 8–25% |
| Soluble silicates (as $Na_2O, 2SiO_2$) | 5–15% |
| Sodium sulfate (as $Na_2SO_4$) | 0–5% |
| Zeolite (as $NaAlSiO_4$) | 15–28% |
| Sodium perborate (as $NaBO_3.4H_2O$) | 0–20% |
| Bleach activator (TAED or NOBS) | 0–5% |
| Enzymes (calculated as pure enzyme protein) | 0.0001–0.1% |
| Minor ingredients (e.g. perfume, optical brighteners) | 0–3% |

13) Detergent formulations as described in 1)–12) wherein all or part of the linear alkylbenzenesulfonate is replaced by ($C_{12}$–$C_{18}$) alkyl sulfate.

14) A detergent composition formulated as a granulate having a bulk density of at least 600 g/l comprising

| ($C_{12}$–$C_{18}$) alkyl sulfate | 9–15% |
| Alcohol ethoxylate | 3–6% |
| Polyhydroxy alkyl fatty acid amide | 1–5% |
| Zeolite (as $NaAlSiO_4$) | 10–20% |
| Layered disilicate (e.g. SK56 from Hoechst) | 10–20% |
| Sodium carbonate (as $Na_2CO_3$) | 3–12% |
| Soluble silicate (as $Na_2O, 2SiO_2$) | 0–6% |
| Sodium citrate | 4–8% |
| Sodium percarbonate | 13–22% |
| TAED | 3–8% |
| Polymers (e.g. polycarboxylates and PVP) | 0–5% |

-continued

| Enzymes (calculated as pure enzyme protein) | 0.0001–0.1% |
| Minor ingredients (e.g. optical brightener, photo bleach, perfume, suds suppressors) | 0–5% |

15) A detergent composition formulated as a granulate having a bulk density of at least 600 g/l comprising

| ($C_{12}$–$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O, 2SiO_2$) | 0–4% |
| Sodium percarbonate | 13–22% |
| TAED | 1–8% |
| Carboxymethyl cellulose | 0–3% |
| Polymers (e.g. polycarboxylates and PVP) | 0–3% |
| Enzymes (calculated as pure enzyme protein) | 0.0001–0.1% |
| Minor ingredients (e.g. optical brightener, phosphonate, perfume) | 0–3% |

16) Detergent formulations as described in 1)–15) which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12) 14) and 15) which additionally contain a manganese catalyst. The manganese catalyst may, e.g., be one of the compounds described in "Efficient manganese catalysts for low-temperature bleaching", Nature 369, 1994, pp. 637–639.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

Particular forms of dishwashing detergent compositions within the scope of the invention include:

1) POWDER AUTOMATIC DISHWASHING COMPOSITION

| Nanionic surfactant | 0.4–2.5% |
| Sodium metasilicate | 0–20% |
| Sodium disilicate | 3–20% |
| Sodium triphosphate | 20–40% |
| Sodium carbonate | 0–20% |
| Sodium perborate | 2–9% |
| Tetraacetylethylenediamine (TAED) | 1–4% |
| Sodium sulphate | 5–33% |
| Enzymes | 0.0001–0.1 |

2) POWDER AUTOMATIC DISHWASHING COMPOSITION

| Nonionic surfactant (e.g. alcohol ethoxylate) | 1–2% |
| Sodium disilicate | 2–30% |
| Sodium carbonate | 10–50% |
| Sodium phosphonate | 0–5% |

| | |
|---|---|
| Trisodium citrate dihydrate | 9–30% |
| Nitrilotrisodium acetate (NTA) | 0–20% |
| Sodium perborate monohydrate | 5–10% |
| Tetraacetylethylenediamine (TAED) | 1–2% |
| Polyacrylate polymer (e.g. maleic acid/acrylic acid co-polymer) | 6–25% |
| Enzymes | 0.0001–0.1% |
| Perfume | 0.1–0.5% |
| Water | 5–10 |

3) POWDER AUTOMATIC DISHWASHING COMPOSITION

| | |
|---|---|
| Nonionic surfactant | 0.5–2.0% |
| Sodium disilicate | 25–40% |
| Sodium citrate | 30–55% |
| Sodium carbonate | 0–29% |
| Sodium bicarbonate | 0–20% |
| Sodium perborate monohydrate | 0–15% |
| Tetraacetylethylenediamine (TAED) | 0–6% |
| Maleic acid/acrylic acid copolymer | 0–5% |
| Clay | 1–3% |
| Poly(amino acids) | 0–20% |
| Sodium polyacrylate | 0–8% |
| Enzymes | 0.0001–0.1% |

4) POWDER AUTOMATIC DISHWASHING COMPOSITION

| | |
|---|---|
| Nonionic surfactant | 1–2% |
| Zeolite MAP | 15–42% |
| Sodium disilicate | 30–34% |
| Sodium citrate | 0–12% |
| Sodium carbonate | 0–20% |
| Sodium perborate monohydrate | 7–15% |
| Tetraacetylethylenediamine (TAED) | 0–3% |
| Polymer | 0–4% |
| Maleic acid/acrylic acid copolymer | 0–5% |
| Organic phosphonate | 0–4% |
| Clay | 1–2% |
| Enzymes | 0.0001–0.1% |
| Sodium sulphate | Balance |

5) POWDER AUTOMATIC DISHWASHING COMPOSITION

| | |
|---|---|
| Nonionic surfactant | 1–7% |
| Sodium disilicate | 18–30% |
| Trisodium citrate | 10–24% |
| Sodium carbonate | 12–20% |
| Monopersulphate (2 $KHSO_5 \cdot KHSO_4 \cdot K_2SO_4$) | 15–21% |
| Bleach stabilizer | 0.1–2% |
| Maleic acid/acrylic acid copolymer | 0–6% |
| Diethylenetriaminepentaacetate, pentasodium salt | 0–2.5% |
| Enzymes | 0.0001–0.1% |
| Sodium sulphate, water | Balance |

6) POWDER AND LIQUID DISHWASHING COMPOSITION WITH CLEANING SURFACTANT SYSTEM

| | |
|---|---|
| Nonionic surfactant | 0–1.5% |
| Octadecyl dimethylamine N-oxide dihydrate | 0–5% |
| 80:20 wt.C18/C16 blend of octadecyl dimethylamine N-oxide dihydrate and hexadecyldimethyl amine N-oxide dihydrate | 0–4% |
| 70:30 wt.C18/C16 blend of octadecyl bis (hydroxyethyl)amine N-oxide anhydrous and hexadecyl bis (hydroxyethyl)amine N-oxide anhydrous | 0–5% |
| $C_{13}$–$C_{15}$ alkyl ethoxysulfate with an average degree of ethoxylation of 3 | 0–10% |
| $C_{12}$–$C_{15}$ alkyl ethoxysulfate with an average degree of ethoxylation of 3 | 0–5% |
| $C_{13}$–$C_{15}$ ethoxylated alcohol with an average degree of ethoxylation of 12 | 0–5% |
| A blend of $C_{12}$–$C_{15}$ ethoxylated alcohols with an average degree of ethoxylation of 9 | 0–6.5% |
| A blend of $C_{13}$–$C_{15}$ ethoxylated alcohols with an average degree of ethoxylation of 30 | 0–4% |
| Sodium disilicate | 0–33% |
| Sodium tripolyphosphate | 0–46% |
| Sodium citrate | 0–28% |
| Citric acid | 0–29% |
| Sodium carbonate | 0–20% |
| Sodium perborate monohydrate | 0–11.5% |
| Tetraacetylethylenediamine (TAED) | 0–4% |
| Maleic acid/acrylic acid copolymer | 0–7.5% |
| Sodium sulphate | 0–12.5% |
| Enzymes | 0.0001–0.1% |

7) NON-AQUEOUS LIQUID AUTOMATIC DISHWASHING COMPOSITION

| | |
|---|---|
| Liquid nonionic surfactant (e.g. alcohol ethoxylates) | 2.0–10.0% |
| Alkali metal silicate | 3.0–15.0% |
| Alkali metal phosphate | 20.0–40.0% |
| Liquid carrier selected from higher glycols, polyglycols, polyoxides, glycolethers | 25.0–45.0% |
| Stabilizer (e.g. a partial ester of phosphoric acid and a $C_{16}$–$C_{18}$ alkanol) | 0.5–7.0% |
| Foam suppressor (e.g. silicone) | 0–1.5% |
| Enzymes | 0.0001–0.1% |

8) NON-AQUEOUS LIQUID DISHWASHING COMPOSITION

| | |
|---|---|
| Liquid nonionic surfactant (e.g. alcohol ethoxylates) | 2.0–10.0% |
| Sodium silicate | 3.0–15.0% |
| Alkali metal carbonate | 7.0–20.0% |
| Sodium citrate | 0.0–1.5% |
| Stabilizing system (e.g. mixtures of finely divided silicone and low molecular weight dialkyl polyglycol ethers) | 0.5–7.0% |
| Low molecule weight polyacrylate polymer | 5.0–15.0% |
| Clay gel thickener (e.g. bentonite) | 0.0–10.0% |
| Hydroxypropyl cellulose polymer | 0.0–0.6% |
| Enzymes | 0.0001–0.1% |
| Liquid carrier selected from higher lycols, polyglycols, polyoxides and glycol ethers | Balance |

9) THIXOTROPIC LIQUID AUTOMATIC DISHWASHING COMPOSITION

| | |
|---|---|
| $C_{12}$–$C_{14}$ fatty acid | 0–0.5% |
| Block co-polymer surfactant | 1.5–15.0% |
| Sodium citrate | 0–12% |
| Sodium tripolyphosphate | 0–15% |
| Sodium carbonate | 0–8% |
| Aluminum tristearate | 0–0.1% |
| Sodium cumene sulphonate | 0–1.7% |
| Polyacrylate thickener | 1.32–2.5% |
| Sodium polyacrylate | 2.4–6.0% |
| Boric acid | 0–4.0% |
| Sodium formate | 0–0.45% |
| Calcium formate | 0–0.2% |
| Sodium n-decydiphenyl oxide disulphonate | 0–4.0% |
| Monoethanol amine (MEA) | 0–1.86% |
| Sodium hydroxide (50%) | 1.9–9.3% |
| 1,2-Propanediol | 0–9.4% |
| Enzymes | 0.0001–0.1% |
| Suds suppressor, dye, perfumes, water | Balance |

10) LIQUID AUTOMATIC DISHWASHING COMPOSITION

| | |
|---|---|
| Alcohol ethoxylate | 0–20% |
| Fatty acid ester sulphonate | 0–30% |
| Sodium dodecyl sulphate | 0–20% |
| Alkyl polyglycoside | 0–21% |
| Oleic acid | 0–10% |
| Sodium disilicate monohydrate | 18–33% |
| Sodium citrate dihydrate | 18–33% |
| Sodium stearate | 0–2.5% |
| Sodium perborate monohydrate | 0–13% |
| Tetraacetylethylenediamine (TAED) | 0–8% |
| Maleic acid/acrylic acid copolymer | 4–8% |
| Enzymes | 0.0001–0.1% |

11) LIQUID AUTOMATIC DISHWASHING COMPOSITION CONTAINING PROTECTED BLEACH PARTICLES

| | |
|---|---|
| Sodium silicate | 5–10% |
| Tetrapotassium pyrophosphate | 15–25% |
| Sodium triphosphate | 0–2% |
| Potassium carbonate | 4–8% |
| Protected bleach particles, e.g. chlorine | 5–10% |
| Polymeric thickener | 0.7–1.5% |
| Potassium hydroxide | 0–2% |
| Enzymes | 0.0001–0.1% |
| Water | Balance |

11) Automatic dishwashing compositions as described in 1), 2), 3), 4), 6) and 10), wherein perborate is replaced by percarbonate.

12) Automatic dishwashing compositions as described in 1)–6) which additionally contain a manganese catalyst. The manganese catalyst may, e.g., be one of the compounds described in "Efficient manganese catalysts for low-temperature bleaching", Nature 369, 1994, pp. 637–639.

The α-amylases of the invention may be incorporated in concentrations conventionally employed in detergents. It is at present contemplated that, in the detergent composition of the invention, the α-amylase may be added in an amount corresponding to 0.00001–1 mg (calculated as pure enzyme protein) of α-amylase per liter of wash/dishwash liquor.

The present invention is further illustrated in the following examples which are not intended to be in any way limiting to the scope of the invention as claimed.

EXAMPLE 1

α-amylase Preparations from Bacillus strains NCIB 12289, NCIB 12513, DSM 9375 and NCIB 12512.

Fermentation:

Each of the above mentioned Bacillus strains was incubated at 26° C. on a rotary shaking table (300 r.p.m.) in 500 ml baffled Erlenmeyer flasks containing 100 ml of BP-X medium+0.1 M Carbonate buffer pH 9.0.

| | |
|---|---|
| Potato starch | 100 g |
| Ground barley | 50 g |
| Soybean flour | 20 g |
| Sodium caseinate | 10 g |
| $Na_2HPO_4 \times 12\ H_2O$ | 9 g |
| Termamyl ® 60L* | 0.1 g |
| Pluronic ® | 0.1 g |

*available from Novo Nordisk A/S.

The starch in the medium was liquified by slowly heating the medium from 60° C. to 85° C. for 30 minutes. After this the temperature of the medium was quickly raised to 95° C. for 10 minutes and then cooled. Lastly the medium was sterilized by heating at 121° C. for 40 minutes.

Purification of α-amylase from NCIB 12289, DSM 9375 and NCIB 12512.

After 5 days of incubation the culture broth was filtrated and concentrated using a Filtron™ ultrafiltration module with 3 KD membranes and washed with deionized water until the conductivity was 1 mS/cm. The pH was adjusted to pH 5.9. with 10% (v/v) acetic acid. A S-sepharose FF column was equilibrated in EKV-buffer, pH 5.9. If not otherwise stated, the purification buffer was 100 mM boric acid, 10 mM succinic acid, 2 mM $CaCl_2$, (EKV-buffer) adjusted to the indicated pH with NaOH.

The enzyme solution was applied to the column, the column was washed with EKV-buffer, pH 5.9, and the amylase was eluted with a linear NaCl gradient (0→500 mM NaCl). Amylase containing fractions were pooled and the pH adjusted to pH 7 with 3% (w/v) NaOH.

A chelate agarose column was loaded with Cu++ and equilibrated in the following manner: 50 mM $CuSO_4$, pH 5 was pumped on to the column until the whole column was blue, then excess of Cu++-ions were removed by washing the column with 500 mM imidazol, pH 7, and finally the column was equilibrated with EKV-buffer, pH 7. The amylase pool from the S-sepharose column was applied to the Cu++-loaded Chelate agarose column, the column was washed with EKV-buffer, pH 7, and the enzyme was eluted with a linear gradient of imidazol (0→500 mM imidazol). Amylase containing fractions were pooled and a solution of saturated ammonium sulphate was added to give a final concentration of 1M $(NH_4)_2SO_4$ in the pool.

A phenyl sepharose column was equilibrated in EKV-buffer+1M $(NH_4)_2SO_4$, pH 7. The amylase pool from the Cu++-column was applied to the hydrophobic interaction column. Binding experiments had shown that the amylase is a rather hydrophobic enzyme, and hence binds tightly to the phenyl column. Protein which did not bind as tightly to the column was washed off the column with EKV-buffer, pH 7. The amylase was step-eluted from the column with EKV-buffer +25% (v/v) isopropanol. The amylase containing pool was adjusted to pH 9.5 with 3% (w/v) NaOH and diluted 5 times with deionized water.

A Q-sepharose HP column was equilibrated in 20 mM Tris-HCl, pH 9.5. The amylase pool from the phenyl sepharose column was applied to the column and the column was washed with 20 mM Tris-HCl, pH 9.5. The amylase was eluted with a linear gradient of NaCl (0→250 mM NaCl).

The amylase peak was adjusted to pH 7 with 10% (v/v) acetic acid.

A Cu++-loaded chelating sepharose FF column (loaded with Cu++ as described for the chelate agarose column) was equilibrated with EKV-buffer, pH 7. The amylase peak from the Q-sepharose column was applied to the column, and the column was washed thoroughly with EKV-buffer, pH 7. The amylase was eluted with a steep linear gradient of imidazol (0→500 mM imidazol).

The purified amylase was purity checked by SDS-PAGE electrophoresis. The coomassie stained gel had only one band.

Purification of α-amylase from NCIB 12513

After 5 days of incubation the culture broth was filtrated and concentrated using a Filtron™ ultrafiltration module with 3 KD membranes. The concentrated solution was filtrated and saturated to 20% w/w with ammoniumsulfate. The solution was then batch absorbed using a AFFI-T™ matrix from Kem-En-Tec A/S. The amylase was eluted using 25% isopropanol in 20 mM Tris pH 7.5 after wash of the matrix with deionized water. The eluted enzyme was subjected to dialysis (20 mM Tris pH 8.5) and a stepwise batch adsorption on Q-sepharose FF for colour removal was made.

A chelate agarose column was loaded with Cu++ and equilibrated in the following manner: 50 mM $CuSO_4$, pH 5 was pumped on to the column until the whole column was blue, then excess of Cu++-ions was removed by washing the column with 500 mM imidazol, pH 7, and finally the column was equilibrated with 50 mM borate buffer, pH 7.

In spite of the low pI (5.8) the amylase was not bound to the Q-sepharose FF at pH 8.5.

The run through from the Q-sepharose FF column was applied on the Cu-chelating agarose and eluted using 250 mM imidazol, 20 mM Tris pH 7.0 and the eluted column was dialysed against 50 mM borate buffer pH 7.0. The pH was adjusted to pH 9.5 and the dialysed solution was bound on a Q-sepharose HP and eluted over 10 columns using a linear gradient from 0–250 mM NaCl. Amylase containing fractions were pooled and a solution of saturated ammonium sulphate was added to give a final concentration of 20% w/w, and the fractions were applied on a phenyl sepharose column. The column was washed using deionized water and eluted using 25% isopropanol in 50 mM borate buffer pH 7.0.

The purified amylase was purity checked by SDS-PAGE electrophoresis. The coomassie stained gel had only one band.

EXAMPLE 2

Physical-Chemical Properties of the α-Amylases

The α-amylase obtained from Bacillus strain NCIB 12289, fermented and purified as described in Example 1, was found to possess the following properties:

A pI of about 8.8–9.0 as determined by isoelectric focusing on LKB Ampholine® PAG plates (3.5–9.5)—meaning that said plates are useful in the pi range of 3.5 to 9.5.

A molecular weight of approximately 55 kD as determined by SDS-PAGE.

A pH profile as shown in FIG. 1, which was determined at 37° C. in the pH range of from 4 to 10.5. The assay for α-amylase activity described previously was used, using Britton-Robinson buffer adjusted to predetermined pH values. It appears from FIG. 1 that the enzyme possesses α-amylase activity at all pH values of from 4 to 10.5, having optimum at pH 7.5–8.5, and at least 60% of the maximum activity at pH 9.5.

Amino acid sequence of the α-amylase was determined using standard methods for obtaining and sequencing peptides, for reference see Findlay & Geisow (Eds.), *Protein Secuencing - a Practical Approach,* 1989, IRL Press.

The N-terminal amino acid sequence was found to be His-His-Asn-Gly-Thr-Asn-Gly-Thr-Met-Met-Gln-Tyr-Phe-Glu-Trp-Tyr-Leu-Pro-Asn-Asp (SEQ ID No. 3).

The α-amylases obtained from Bacillus strains NCIB 12512 and DSM 9375, fermented and purified as described in Example 1, were found to possess the same pI (8.8–9.0), the same molecular weight (55 kD), and the same N-terminal sequence (SEQ-ID No. 3) as the α-amylase obtained from NCIB 12289; so it can be concluded that the α-amylases obtained from NCIB 12289, NCIB 12512 and DSM 9375 have the following common features:

(a) A pI of about 8.6–9.3 determined by isoelectric focusing on LKB Ampholine® PAG plates;

b) A molecular weight of approximately 55 kD as determined by SDS-PAGE;

c) An N-terminal amino acid with the amino acid sequence as shown in ID No. 3.

The full amino acid sequence of the Bacillus strain NCIB 12512 α-amylase is disclosed in SEQ ID No. 1 of the present invention. The full DNA sequence of the Bacillus strain NCIB 12512 α-amylase is disclosed in SEQ ID No. 4 of the present invention.

The α-amylase obtained from Bacillus strain NCIB 12513, fermented and purified as described in Example 1, was found to possess a pI of about 5.8 and a molecular weight of approximately 55 kD.

The full amino acid sequence of the Bacillus strain NCIB 12513 α-amylase is disclosed in SEQ ID No. 2 of the present invention. The full DNA sequence of the Bacillus strain NCIB 12513 α-amylase is disclosed in SEQ ID No. 5 of the present invention.

EXAMPLE 3 pH and Temperatures Profiles of the α-Amylases According to the Invention Compared to Termamyl®.

Figure 2:
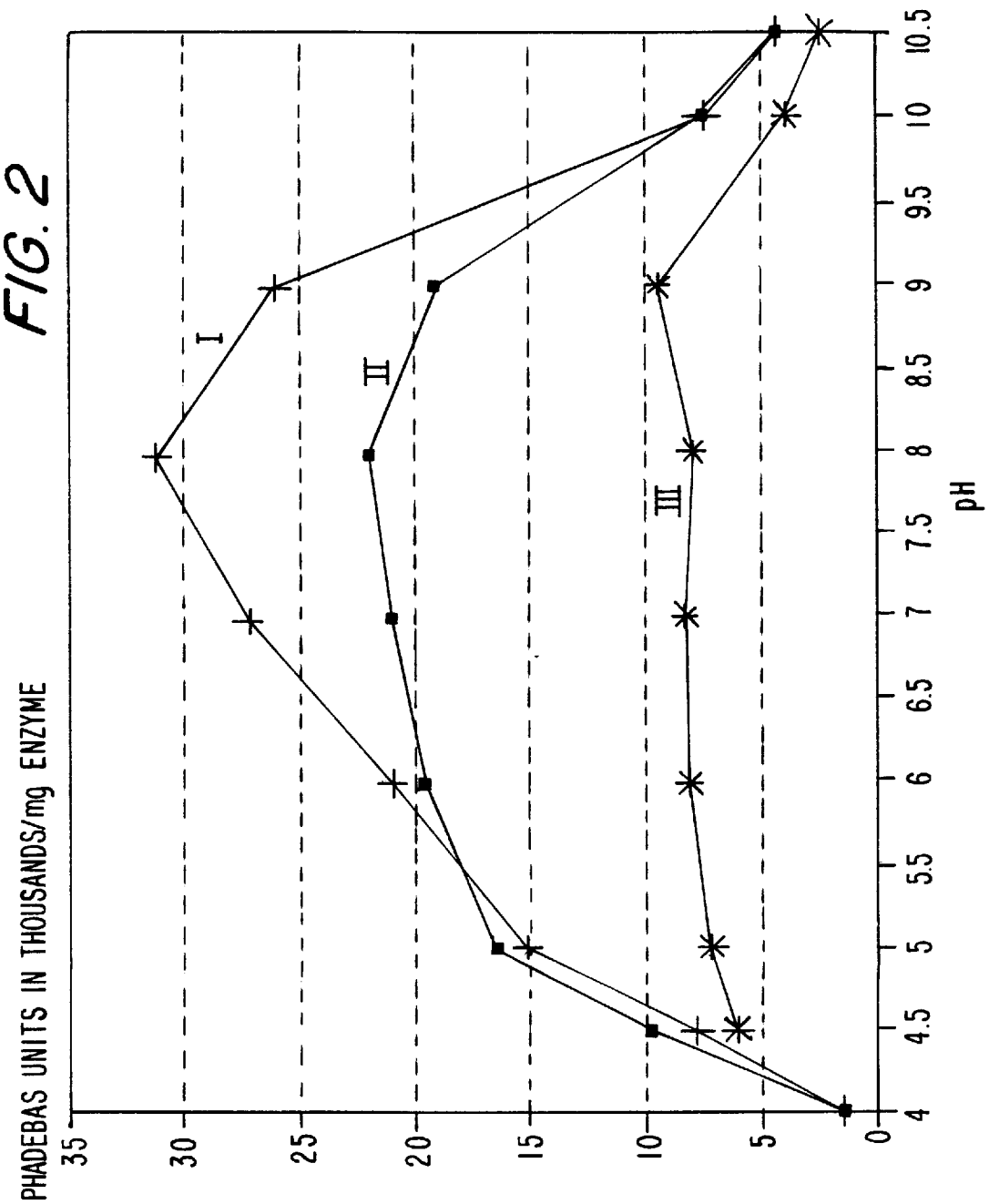
FIG. 2 shows the pH profile of an α-amylase obtained from Bacillus strain NCIB 12512 (I), of an α-amylase obtained from Bacillus strain NCIB 12513 (II) and of Termamyl® (III) determined at 55° C. in the pH interval of from 4 to 10.5, the test being performed as described in Example 3.

A pH profile of an α-amylase obtained from Bacillus strain NCIB 12512 (I), of an α-amylase obtained from Bacillus strain NCIB 12513 (II) and of Termamyl® (III) were determined. at 55° C. in the pH interval of from 4 to 10.5. The α-amylases of the invention were fermented and purified as described in Example 1 and Termamyl® was obtained from Novo Nordisk A/S. The assay for α-amylase activity described previously was used, using 50 mM Britton-Robinson buffer adjusted to predetermined pH values and a reaction time of 15 minutes. The results are presented in FIG. 2. It appears from FIG. 2 that the α-amylases of the invention possess α-amylase activity at all pH values of from pH 4 to pH 10.5, having optimum at pH 7.5–8.5.

A temperature profile of an α-amylase obtained from Bacillus strain NCIB 12512 (I), of an α-amylase obtained from Bacillus strain NCIB 12513 (II) and of Termamyl® (III) were determined at pH 10.0 in the temperature interval of from 25° C. to 95° C. The α-amylases of the invention were fermented and purified as described in Example 1 and Termamyl® was obtained from Novo Nordisk A/S. The assay for α-amylase activity described previously was used, using 50 mM Britton-Robinson buffer adjusted to pH 10.0 and a reaction time of 10 minutes. The results are presented in FIG. 3. It appears from FIG. 3 that the α-amylases of the invention possess α-amylase activity at all temperature values of from 25° C. to 85° C., having optimum at 45° C.–55° C., and that the specific activity of the α-amylase of the invention is 25% higher than the specific activity of Termamyl® at any temperature in the temperature interval of from 25° C. to 55° C.

EXAMPLE 4

Dishwashing Performance of Novel α-amylases

α-amylases of the invention obtained from Bacillus strain NCIB 12289 and from Bacillus strain 12512 as described in Example 1, were tested using the following test for detergent amylases for automatic dishwashing:

Plates were dipped in hot corn starch and glasses were soiled by pouring corn starch from one glass to another. The plates and glasses were left to dry overnight and then washed in a dishwasher under the following conditions:

| Amylase dosage: | 0–0.50 mg of enzyme protein per liter of washing liquor |
| --- | --- |
| Detergent: | Commercial European |
| Detergent dosage: | 4.0 g per liter of washing liquor |
| Dishwashing: | 45° C., 55° C. or 65° C. program, Cylinda |
| pH: | 10.1 during dishwashing. |

Evaluation/Rating System:

Removal of starch film (RSF) from the plates and glasses was evaluated after colouring the items with iodine (iodine turns starch blue). The following rating scale was used:

| Rating | Dishware | Glassware |
| --- | --- | --- |
| 6 | clean | clean |
| 5 | spots | thin |
| 4 | thin | moderate |
| 3 | moderate | heavy |
| 2 | heavy | very heavy |
| 1 | very heavy | extreme heavy |
| 0 | blind* | blind. |

*unwashed

After each item had been evaluated according to the above mentioned rating system, the total value of the scores obtained was divided by the total number of items. The resulting RSF-value was then plotted against the mg α-amylase protein used per liter of washing liquor.

Figure 4:
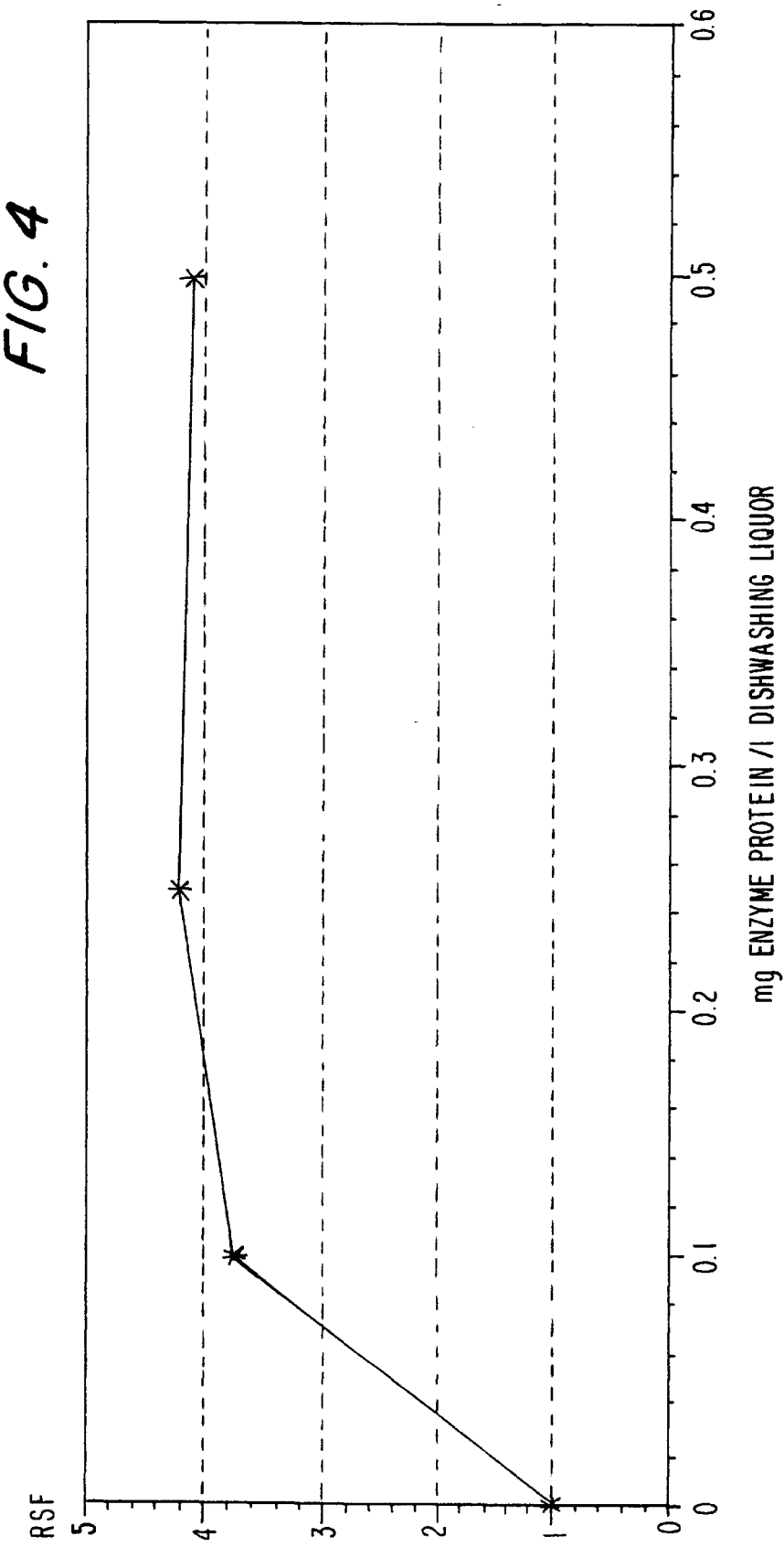
FIG. 4 shows the RSF-rating—removal of starch film from dish- and glassware, as a function of the dosage of a novel α-amylase (obtained from Bacillus strain NCIB 12289) at 55° C., the test being performed as described in Example 4.

Results:

Bacillus strain NCIB 12289 α-amylase: This α-amylase was tested at 55° C. and the results are shown in FIG. 4. It can be seen from FIG. 4 that an RSF value of between 3 and 4 is obtained at an enzyme dosage of 0.1 mg of α-amylase protein per liter of washing liquor.

Figure 5:
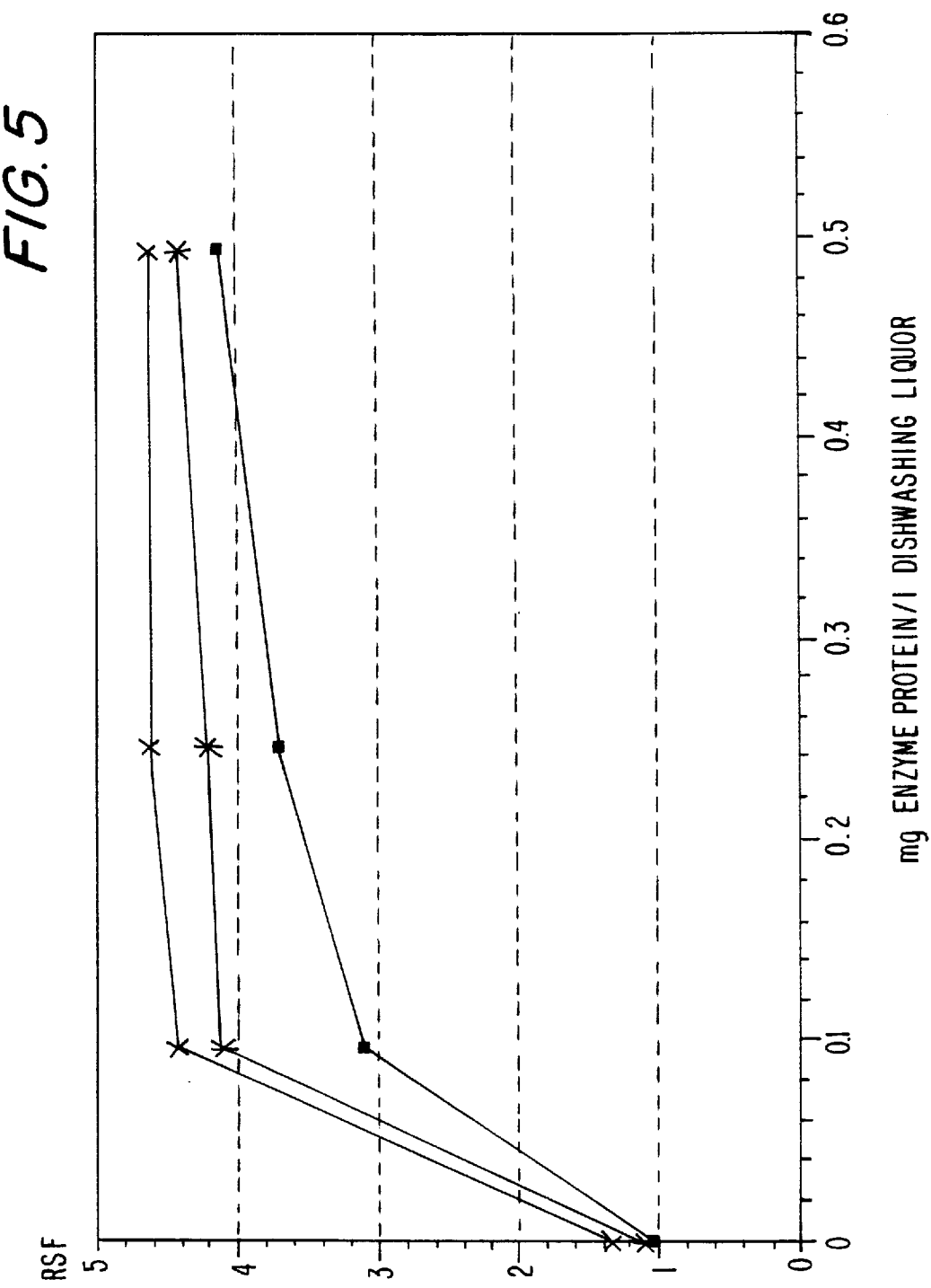
FIG. 5 shows the RSF-rating—removal of starch film from dish- and glassware, as a function of the dosage of a novel α-amylase (obtained from Bacillus strain NCIB 12512) at 45° C. (•), at 55° C. (*) and at 65° C. (x), the test being performed as described in Example 4.

Bacillus strain NCIB 12512 α-amylase: This α-amylase was tested at 45° C. (•), at 55° C. (*) and at 65° C. (x), and the results are shown in FIG. 5. It can be seen from FIG. 5 that an RSF value of between 3 and 4.5 is obtained at an enzyme dosage of 0.1 mg of α-amylase protein per liter of washing liquor (the RSF-value increasing with increasing temperature).

EXAMPLE 5

Mini Dishwashing Performance of Novel α-Amylases

The following mini dishwashing assay was used: A suspension of starchy material was boiled and cooled to 20° C. The cooled starch suspension was applied on small, individually identified glass plates (approx. 2×2 cm) and dried at a temperature in the range of 60°–140° C. in a drying cabinet. The individual plates were then weighed. For assay purposes, a solution of standard European-type automatic dishwashing detergent (5 g/l) having a temperature of 55° C. was prepared. The detergent was allowed a dissolution time of 1 minute., after which the amylase in question was added to the detergent solution (contained in a beaker equipped with magnetic stirring) so as to give an enzyme concentration of 0.5 mg/l. At the same time, the weighed glass plates, held in small supporting clamps, were immersed in a substantially vertical position in the amylase/detergent solution, which was then stirred for 15 minutes at 55° C. The glass plates were then removed from the amylase/detergent solution, rinsed with distilled water, dried at 60° C. in a drying cabinet and re-weighed. The performance of the amylase in question [expressed as an index relative to Termamyl® (index 100)] was then determined from the difference in weight of the glass plates before and after treatment, as follows:

Index=weight loss for plate treated with α-amylase/weight loss for plate treated with Termamyl®          100

Results

The above described mini dishwashing test was performed at pH 10.0 with Termamyl®, the novel α-amylase from NCIB 12513 and the novel α-amylase from NCIB 12512 (the novel α-amylases obtained as described in Example 1). The tests gave the following results:

| Termamyl ® | Index: 100 |
| --- | --- |
| α-amylase (NCIB 12512) | Index: 163 |
| α-amylase (NCIB 12513) | Index: 175 |

Figure 3:
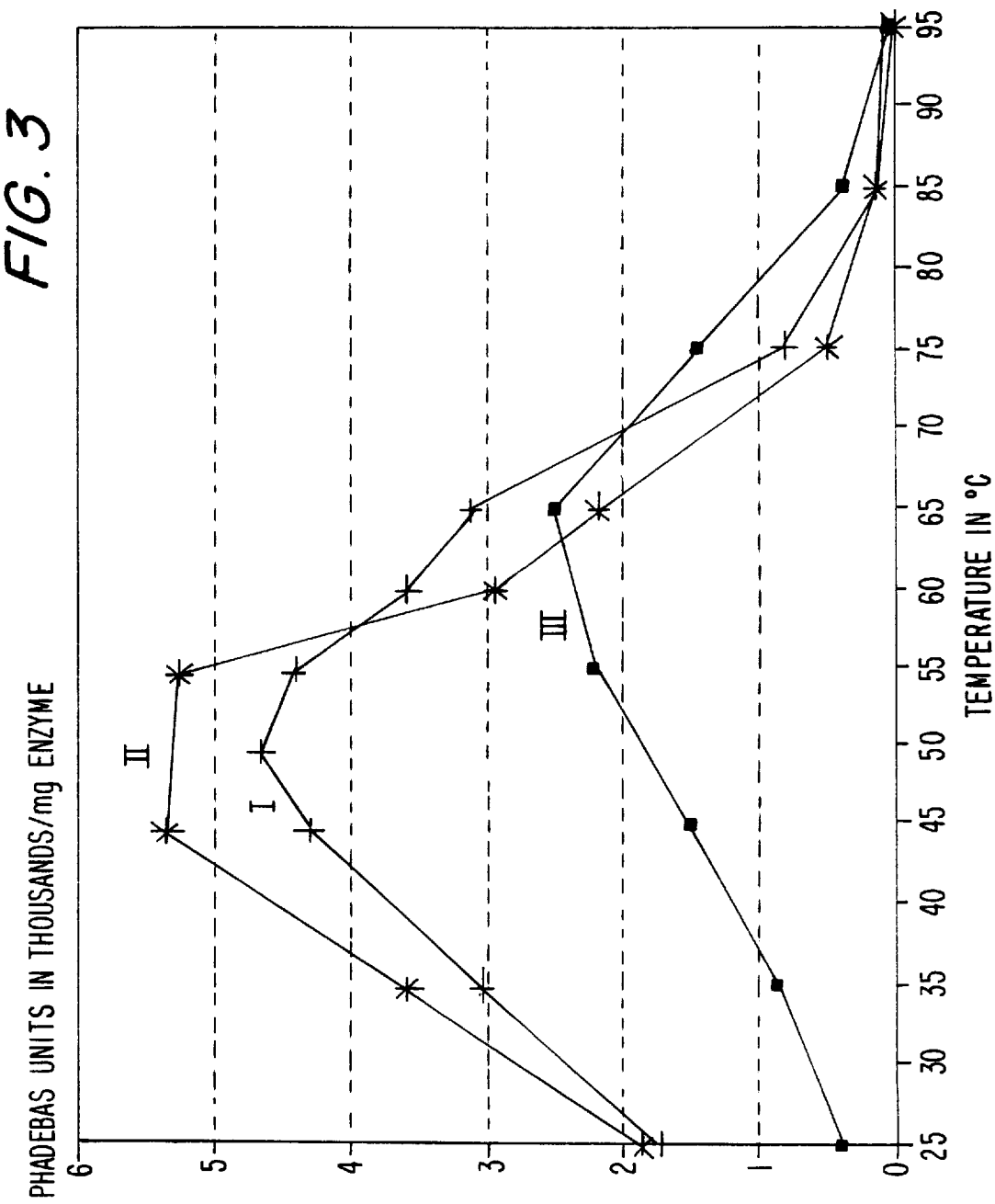
FIG. 3 shows the temperature profile of an α-amylase obtained from Bacillus strain NCIB 12512 (I), of an α-amylase obtained from Bacillus strain NCIB 12513 (II) and of Termamyl® (III) determined at pH 10.0 in the temperature interval of from 25° C. to 95° C., the test being performed as described in Example 3.

Surprisingly, the performance in the mini dishwashing test is proportional with the specific activity at pH 10.0, 55° C. as can be seen from FIG. 3:

| Termamyl ® | Spec. activity: 2200 U/mg |
| --- | --- |
| α-amylase (NCIB 12512) | Spec. activity: 4400 U/mg |
| α-amylase (NCIB 12513) | Spec. activity: 5200 U/mg. |

EXAMPLE 6

| Laundry washing | |
| --- | --- |
| Detergent: | Commercial US heavy duty granulate detergent (HDG) |
| Detergent dosage: | 2 g/l |
| α-amylase dosage: | 0.2 mg enzyme protein/l |
| Soil: | Potato starch colored with Cibacron Blue 3GA on cotton |
| Water hardness: | 9° dH |
| Time: | 15 minutes |
| Temperature: | 40° C. |

Evaluation:

Reflectance at 660 nm. The delta reflectance was calculated from the reflectance obtained for a swatch having been washed with the relevant enzyme and the reflectance obtained for a swatch washed without enzyme. More specifically, the delta reflectance is the reflectance obtained with enzyme minus the reflectance obtained without enzyme.

Results

The above described laundry washing test was performed with Termamyl®, the novel α-amylase from NCIB 12513 and the novel α-amylase from NCIB 12512 (the novel α-amylases obtained as described in Example 1) The tests gave the following results:

| | |
|---|---|
| Termamyl ® | Index: 100 |
| α-amylase (NCIB 12512) | Index: 145 |
| α-amylase (NCIB 12513) | Index: 133 |

From the results presented above it is evident that the α-amylases of the invention exert a considerably improved starch removal capacity relative to Termamyl, in other words that the α-amylases of the invention have an improved laundry washing performance compared to that of Termamyl.

EXAMPLE 7

Catalytic Efficiency of the Bacillus Strain NCIB 12512 α-Amylase and the Bacillus Strain NCIB 12513 α-Amylase Compared with Termamyl®.

The kinetics of hydrolysis catalyzed by the α-amylases of the invention and by Termamyl® at various substrate concentrations were determined using the Somogyi-Nelson method (described below) with amylose (Merck 4561) and amylopectin (Sigma A7780) as substrates.

The hydrolysis velocities were measured under different substrate concentrations (1%, 0.5%, 0.3%, 0.25% and 0.2%).

The number of reducing sugars were measured using the Somogyi-Nelson method, and determined as glucose eqv. made/mg of amylase x h giving the hydrolysis velocity. The data were plotted according to the Michaelis-Menten and Lineweaver-Burk equations. From these equations $V_{max}/K_m$ can easily be calculated by using the following approximation:

$$[S] << K_m: V = V_{max} \times \frac{[S]}{K_m} = \frac{V_{max}}{K_m} \times [S]$$

When $$V = V_{max} \times \frac{[S]}{[S] + K_m}$$

* At a given substrate concentration, that substrate concentration being less than $K_m$, the expression $V_{max}/K_m$ is equivalent to the catalytic efficiency of a given α-amylase. In Table 1 below $V_{max}/K_m$ is calculated for three different α-amylases.

TABLE 1

Catalytic efficiency [$V_{max}/K_m$] determined at 55° C., pH 7.3 in 50 mM Britton-Robinson buffer

| | α-amylase (NCIB 12513) | α-amylase (NCIB 12512) | Termamyl ® |
|---|---|---|---|
| Amylopectin | 11.9 sec$^{-1}$ × [g/l]$^{-1}$ | 11.2 sec$^{-1}$ × [g/l]$^{-1}$ | 3.2 sec$^{-1}$ × [g/l]$^{-1}$ |
| Amylose | 31.3 sec$^{-1}$ × [g/l]$^{-1}$ | 30.2 sec$^{-1}$ × [g/l]$^{-1}$ | 5.4 sec$^{-1}$ × [g/l]$^{-1}$ |

The catalytic efficiency of α-amylase (NCIB 12513) and α-amylase (NCIB 12512) have shown to be surprisingly high towards both Amylopectin and Amylose compared to Termamyl. Especially the high catalytic efficienty towards amylose is considered to be of significant importance for the improved specific activities and dishwash/laundry performance compared to Termamyl.

Linear amylose molecules can align themselves next to each other and form interchain hydrogenbonds through the hydroxyl groups. This network of amylose molecules has crystalline characteristics and are difficult to solubilize and hydrolyze by any known amylase.

Somogyi Method for the Determination of Reducing Sugars

The method is based on the principle that the sugar reduces cupric ions to cuprous oxide which reacts with arsenate molybdate reagent to produce a blue colour which is measured spectrophotometrically. The solution which is to be examined must contain between 50 and 600 mg of glucose per liter.

1 ml of sugar solution is mixed with 1 ml of copper reagent and placed in a boiling water bath for 20 minutes. The resulting mixture is cooled and admixed with 1 ml of Nelson's colour reagent and 10 ml of deionized water. The absorbancy at 520 nm is measured.

In the region 0–2 the absorbance is proportional to the amount of sugar, which may thus be calculated as follows:

$$\text{mg glucose}/l = \frac{100(\text{sample} - \text{blank})}{(\text{standard} - \text{blank})}$$

$$\% \text{ glucose} = \frac{(\text{sample} - \text{blank})}{100(\text{standard} - \text{blank})}$$

REAGENTS

1. Somogyi's copper reagent 35.1 g of $Na_2HPO_4.2H_2O$, and 40.0 g of potassium sodium tartrate ($KNaC_4H_4O_2.4H_2O$) are dissolved in 700 ml of deionized water. 100 ml of 1 N sodium hydroxide and 80 ml of 100 cupric sulphate ($CuSO_4.5H_2O$) are added, 180 g of anhydrous sodium sulphate are dissolved in the mixture, and the volume is brought to 1 liter with deionized water.

2. Nelson's colour reagent 50 g of ammonium molybdate are dissolved in 900 ml of deionized water. Then 42 ml of concentrated sulphuric acid (Merck) are added, followed by 6 g of disodium hydrogen arsenate heptahydrate dissolved in 50 ml of deionized water, and the volume is brought to 1 liter with deionized water.

The solution must stand for 24–48 hours at 37° C. before use. It must be stored in the dark in a brown glass bottle with a glass stopper.

3. Standard 100 mg of glucose (May & Baker, anhydrous) are dissolved in 1 liter of deionized water.

Reference: J. Biol. Chem. 153, 375 (1944)

We claim:

1. A DNA construct comprising a DNA sequence encoding an α-amylase having the same activity as an α-amylase obtained from an alkalophilic Bacillus species, having a molecular weight of approximately 55 kD as determined by SDS-PAGE, a specific activity at least 25% higher than the specific activity of a Bacillus licheniformis α-amylase having the amino acid sequence of SEQ ID NO. 4 at a temperature in the range of 25° C. to 55° C. and at a pH value in the range of 8 to 10, and comprising the amino acid sequence depicted in SEQ ID No. 1 or SEQ ID No. 2.

2. The DNA construct of claim 1, in which said α-amylase is obtained from strains NCIB 12289, NCIB 12512, NCIB 12513 or DSM 9375.

3. The DNA construct of claim 1, in which said α-amylase:
  (a) is obtained from strains NCIB 12289 or NCIB 12512;
  (b) has a pI of about 8.6–9.3 as determined by isoelectric focusing on LKB Ampholine® PAG plates; and
  (c) has an activity optimum in the pH range 7.5–8.5, and at least 60% of the maximum activity at pH 9.5.

4. The recombinant expression vector which carries the DNA construct of claim 1.

5. A cell which is transformed with the DNA construct of claim 1.

6. A cell which is transformed with the recombinant expression vector of claim 1.

7. The cell of claim 6, in which said cell is a microorganism.

8. The cell of claim 6, in which said cell is a bacterium or a fungus.

9. The cell of claim 6, in which said cell is a gram-positive bacterium.

10. The cell of claim 6, in which said cell is a gram-positive bacterium selected from the group consisting of Bacillus subtilis, Bacillus licheniformis, Bacillus lentus, Bacillus brevis, Bacillus stearothermophilus, Bacillus alklophilus, Bacillus amyloliquefaciens, Bacillus coagulans, Bacillus lautus, Bacillus thuringiensis, Streptomyces lividans, and Streptomyces murinus.

11. The cell of claim 6, in which said cell is a gram-negative bacterium.

12. The cell of claim 6, in which said cell is E. coli.

13. A method for producing an alph-amylase comprising culturing the cell of claim 6 under conditions conducive to the production of said alph-amylase and subsequently recovering said alph-amylase from the culture.

* * * * *

UNITED STATES PATENT AND TRADEMARK OFFICE
CERTIFICATE OF CORRECTION

PATENT NO.    : 5,856,164
DATED         : January 5, 1999
INVENTOR(S)   : Ottrup et al.

It is certified that error appears in the above-identified patent and that said Letters Patent is hereby corrected as shown below:

Col. 4, lines 52-53, delete "Amylolicuefaciens" and insert --Amyloliquefaciens--.

Col. 4, line 56, delete "orvzae" and insert --oryzae--.

Col. 5, line 48, delete "Amylolicuefaciens" and insert --Amyloliquefaciens--.

Col. 5, line 49, delete "coaculans" and insert --coagulans--.

Col. 5, line 50, delete "meaterium" and insert --megaterium--.

Col. 5, line 50, delete "thurinciensis" and insert --thuringiensis--.

Col. 10, line 6, delete "$C_4H_5Na_3O_7$" and insert --$C_6H_5Na_3O_7$--.

Col. 19, line 53, delete "pi" and insert --pI--.

Col 23, lines 31-39, delete

" $[S] << K_m : V = V_{max} \times \frac{[S]}{K_m} = \frac{V_{max}}{K_m} \times [S]$ When $$V = V_{max} \times \frac{[S]}{[S]+K_m}$$ ."

and insert

-- * $V = V_{max} \times \frac{[S]}{[S]+K_m}$

When $[S] << K_m : V = V_{max} \times \frac{[S]}{K_m} = \frac{V_{max}}{K_m} \times [S]$ --

UNITED STATES PATENT AND TRADEMARK OFFICE
CERTIFICATE OF CORRECTION

PATENT NO. : 5,856,164
DATED : January 5, 1999
INVENTOR(S) : Ottrup et al.

It is certified that error appears in the above-identified patent and that said Letters Patent is hereby corrected as shown below:

Col. 34, lines 58-59, (New Claim 13), delete "alph-amylase" and insert --alpha-amylase--.

Signed and Sealed this

Fifteenth Day of February, 2000

Attest:

Q. TODD DICKINSON

Attesting Officer

Commissioner of Patents and Trademarks